United States Patent [19]

Saunders

[11] Patent Number: 4,617,930

[45] Date of Patent: Oct. 21, 1986

[54] BLADE STIFFENER

[75] Inventor: Gerald A. B. Saunders, Sydenham, Canada

[73] Assignee: Queen's University at Kingston, Kingston, Canada

[21] Appl. No.: 607,008

[22] Filed: May 16, 1984

[51] Int. Cl.⁴ ............................................. A61B 17/14
[52] U.S. Cl. .................................. 128/317; 30/166 R; 30/348
[58] Field of Search ...................... 128/317, 92 E, 305; 30/348, 346.6, 346.58, 355, 347, 166 R

[56] References Cited

U.S. PATENT DOCUMENTS

| 1,726,241 | 8/1929 | Schubert | 30/166 |
| 4,036,236 | 7/1977 | Rhodes | 128/317 |
| 4,386,609 | 6/1983 | Mongeon | 128/317 |

FOREIGN PATENT DOCUMENTS

| 212250 | 9/1957 | Australia | 30/348 |
| 184722 | 8/1922 | United Kingdom | 30/348 |

Primary Examiner—Michael H. Thaler
Attorney, Agent, or Firm—Richard J. Hicks

[57] ABSTRACT

A simple planar saw blade stiffening element for use with an orthopaedic saw is described, which enables a surgeon to make very accurate bone cuts without flexing of a standard saw blade.

1 Claim, 2 Drawing Figures

BLADE STIFFENER

FIELD OF INVENTION

This invention relates to a saw blade stiffener and more particularly to an oscillating orthopaedic saw blade stiffener.

DISCUSSION OF PRIOR ART

Standard orthopaedic saw blades are fabricated from stainless steel sheet and provide the surgeon with a relatively stable and inflexible blade which is suitable for general orthopaedic surgery. In certain circumstances, however, particularly when cutting irregular hard cortex bone, the blade tends to flex and it becomes impossible to make an accurate bone cut. In certain modern techniques, such as knee replacements using porous coated implant prostheses, it has been found essential that the bone be cut with a degree of accuracy heretofore not found to be necessary or generally achievable. Generally such cuts are made with the aid of a saw jig as described in our copending U.S. application Ser. No. 518,479, filed July 29, 1983, now abandoned, the disclosure of which is incorporated herein by reference. Even in such circumstances, blade flex becomes a significant factor and must be elminated. One approach would, of course, be to employ a thicker saw blade but for various technical reasons this is not generally practical. Attempts have also been made to provide a blade which is thicker at the saw end then at the cutting end but this is difficult and expensive to manufacture and rather wasteful of relatively expensive materials.

OBJECTS OF INVENTION

It is an object of the present invention to provide a saw blade stiffener which may be removably mounted on a standard orthopaedic saw blade for use therewith when particularly accurate saw cuts are to be made.

Thus by one aspect of this invention there is provided a stiffener for use in overlying abutting relationship with an orthopaedic saw blade having a cutting edge at one longitudinal end thereof and means to secure said blade to a saw power unit at the other longitudinal end thereof, said stiffener comprising a planar element adapted to extend in contiguous relationship with said saw blade from said other end thereof to a point intermediate said other end and said cutting edge, and including clip means at said intermediate point to releasably engage said stiffener with said saw blade.

BRIEF DESCRIPTION OF DRAWINGS

The invention will be described in more detail hereinafter with reference to the accompanying drawings in which.

DETAILED DESCRIPTION OF PREFERRED EMBODIMENTS

Figure 1:
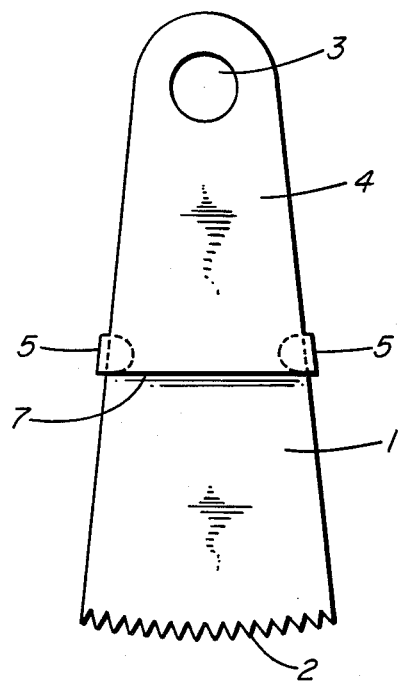
FIG. 1 is a front view of one embodiment of the invention.
Figure 2:
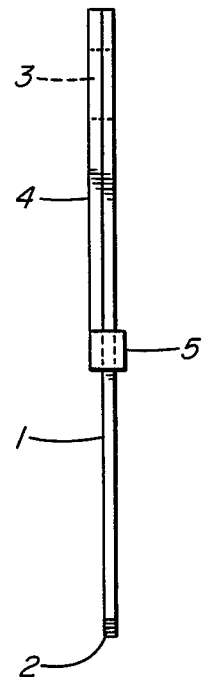
FIG. 2 is a side view of the embodiment of FIG. 1.

In FIG. 1 there is shown a standard segmented orthopaedic saw blade 1 designed for insertion in a standard orthopaedic power saw such as that manufactured by Black and Decker Mfg. Inc. of Towson, Md. Blade 1 is provided with a plurality of cutting teeth 2 at the radial end thereof and a substantially circular hole 3, adjacent the opposite end thereof to receive a clamping boss (not shown) of the saw. A planar stiffening member 4 in overlying close relationship to blade 1 extends from hole 3 generally approximately half the length of the blade towards teeth 2 and is held in close contact with blade 1 by the saw boss at hole 3. The other end of stiffener 4 is held against blade 1 by means of lugs 5, 6 which extend around the sides of the blade 1 from the end 7 of the stiffener 4. With the blade stiffener 4 attached to the blade 1, flexing of blade 1 is minimized and accuracy of the saw cut effected is considerably improved.

It will be appreciated that stiffener 4 may be made from any suitable material, such as stainless steel sheet, which is substantially rigid and which possesses sufficient flexural and tensile strength, and which is not susceptible to atmospheric corrosion and which can withstand the rigours of operating room sterilization procedures.

I claim:

1. A stiffener for use in overlying abutting relationship with an orthopaedic saw blade having a cutting edge at one longitudinal end thereof and hole means adjacent the other longitudinal end thereof adapted to releasably secure said blade to a saw power unit; said stiffener comprising a longitudinal planar element adapted to extend in overlying planar relationship with said saw blade from said other end thereof to a point intermediate said other end and said cutting edge, and including hole means at one end thereof adapted to releasably secure said stiffener to said saw power unit at one end thereof and clip means at the other end thereof to releasably engage said stiffener with said saw blade at said intermediate point.

* * * * *